United States Patent [19]
Fujikawa et al.

[11] 3,957,852
[45] May 18, 1976

[54] DIPHENYL ETHER COMPOUNDS

[75] Inventors: Kanichi Fujikawa, Kyoto; Isao Yokomichi; Nobuyuki Sakashita, both of Kusatsu; Kazuyuki Maeda, Hikone; Takahiro Haga, Kusatsu, all of Japan

[73] Assignee: Ishihara Sangyo Kaisha Ltd., Osaka, Japan

[22] Filed: Dec. 27, 1974

[21] Appl. No.: 537,003

[30] Foreign Application Priority Data
Dec. 27, 1973 Japan.................................. 49-1466

[52] U.S. Cl............................. 260/473 R; 71/108; 260/465 F; 260/501.16; 260/501.17; 260/520 E; 260/544 D; 260/612 D
[51] Int. Cl.²......................................... C07B 69/88

[58] Field of Search..................... 260/473 R, 520 E

[56] References Cited
OTHER PUBLICATIONS
Chem. Abst., Vol. 63, 1965, 1644h.
Chem. Abst. Vol. 63, 1965, 14771G.

*Primary Examiner*—Paul J. Killos
*Attorney, Agent, or Firm*—Sughrue, Rothwell, Mion, Zinn & Macpeak

[57] ABSTRACT

A diphenyl ether compound, such as 2,4′-dichloro-4-trifluoromethyl-3′-carbomethoxydiphenyl ether, which has herbicidal properties and is effective for controlling weeds using soil and/or foliage application and herbicidal compositions containing the same.

13 Claims, No Drawings

DIPHENYL ETHER COMPOUNDS

BACKGROUND OF THE INVENTION

1. FIELD OF THE INVENTION

This invention relates to diphenyl ether compounds and to a herbicidal composition containing at least one diphenyl ether compound as an active ingredient. The diphenyl ether compounds and herbicidal compositions containing the same are effective for controlling various kinds of weeds.

2. DESCRIPTION OF THE PRIOR ART

Various diphenyl ether type herbicidal compounds have been disclosed in, e.g., U.S. Pat. Nos. 3,080,225, 3,316,080, 3,776,961, 3,784,635, and 3,798,276. However, these types of diphenyl ether compounds have a quite different herbicidal effect and the nature of the herbicidal activity for compounds having slightly different structures can vary greatly and thus cannot be predicted from chemical structural considerations.

SUMMARY OF THE INVENTION

The present invention provides diphenyl ether compounds of the following formula (I)

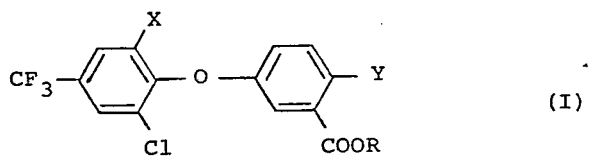

(I)

wherein X is a hydrogen atom or a chlorine atom; Y is a halogen atom; and R is a hydrogen atom, an alkyl group containing 1 to 5 carbon atoms, or a cation, and herbicidal compositions comprising as an active ingredient at least one compound of the formula (I).

DETAILED DESCRIPTION OF THE INVENTION

In the above formula, X is preferably a hydrogen atom, and Y is preferably a chlorine atom or a bromine atom. Further, suitable alkyl groups having 1 to 5 carbon atoms represented by R are a methyl, ethyl, propyl, butyl or pentyl group.

The cations represented by R in the above formula are a salt-forming atom or a salt-forming residue, for example, an alkali metal such as sodium or potassium, and an amine such as a mono- or di-alkylamine having 1 to 5 carbon atoms in the alkyl moieties thereof or a mono- or di-alkanolamine having 1 to 5 carbon atoms in the alkanol moieties thereof.

The diphenyl ether compounds represented by the above general formula exhibit superior growth-inhibiting activities against barnyard grasses which are noxious weeds in crop cultivation, irrespective of whether these weeds are growing in aquatic rice paddies or farm lands or fields, and of whether these compounds are used for soil treatment or foliage treatment. These compounds are also effective for controlling other various weeds in general.

Other than the compounds represented by the above general formula, compounds where R is an alkenyl or alkynyl group such as an allyl group, or an alkoxyalkyl group such as a n-butoxyethyl group can also be expected to be active.

The herbicidal compounds in accordance with this invention can be prepared by any of the following methods.

Method (I):

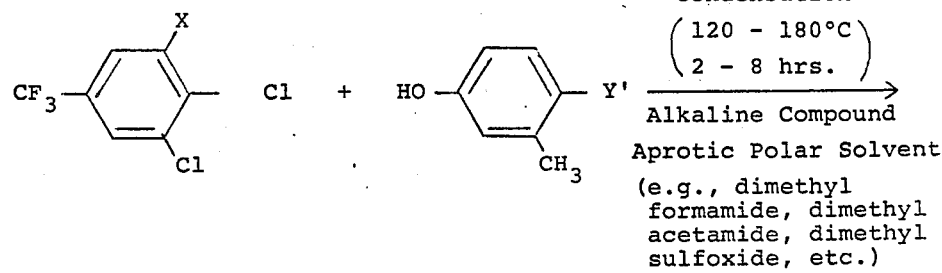

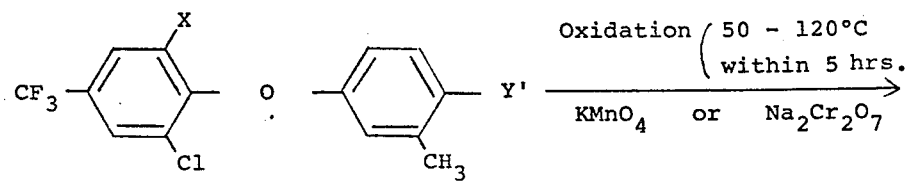

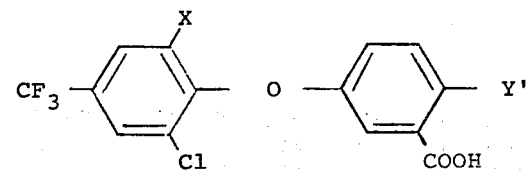

Method (II):

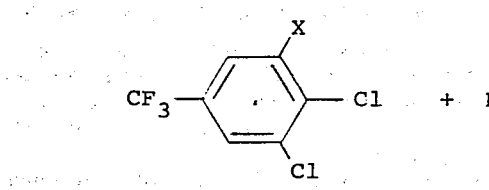 + 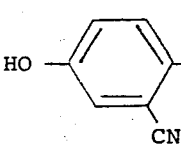 $\xrightarrow[\text{Alkaline Compound}]{\text{Condensation}\begin{pmatrix}120-180°C\\2-8\text{ hrs.}\end{pmatrix}}$ Aprotic Polar Solvent
(e.g., dimethyl formamide, dimethyl acetamide, dimethyl sulfoxide, etc.)

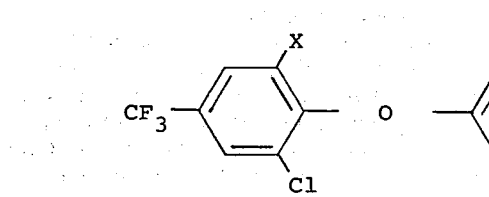 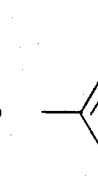 $\xrightarrow[\text{Hydrogen Halide (e.g., HCl)}]{\text{Hydrolysis}\begin{pmatrix}100-130°C\\10-50\text{ hrs.}\end{pmatrix}}$

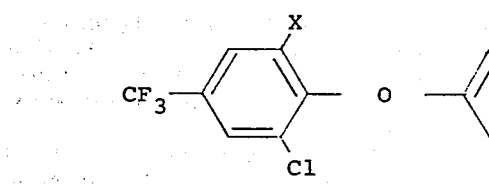 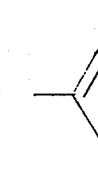

Method (III):

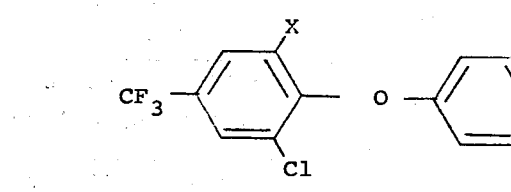 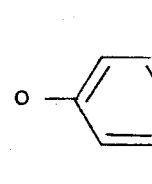 $\xrightarrow[Y_2 \text{ or } SO_2Y_2]{\text{Halogenation}\begin{pmatrix}50-120°C\\0.5-5\text{ hrs.}\end{pmatrix}}$

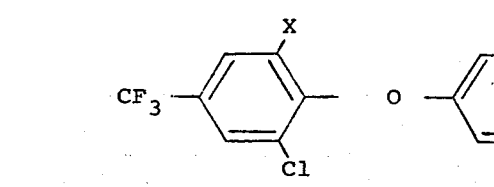 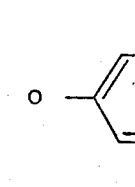

Of the starting materials in this invention, the compounds where R' is an alkyl group having 1 to 5 carbon atoms can be obtained by esterifying the

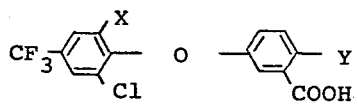

compound which can be produced according to the Method (I) or (II) as described above, according to the following Method (IV). Further in the above Methods (I) and (II), the starting material

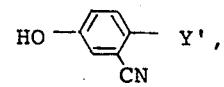

is well known in the art.

Method (IV):

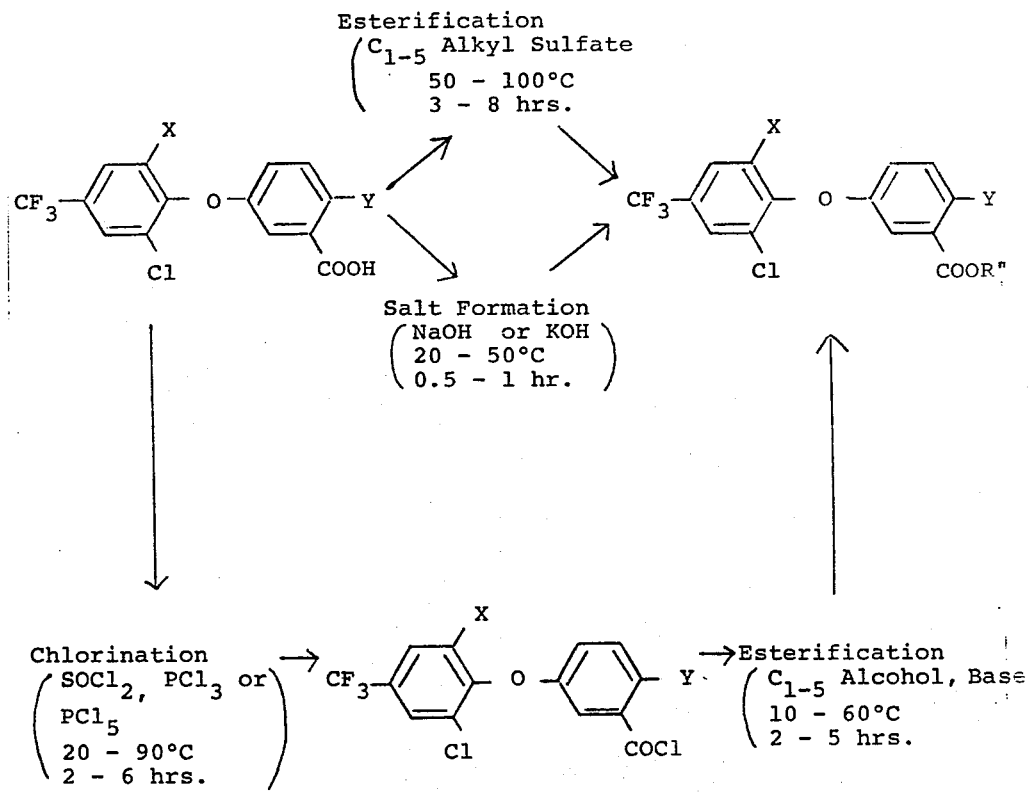

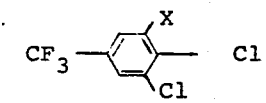

can be prepared according to the method described in Chemical Abstracts, 69, 107614e, the starting material,

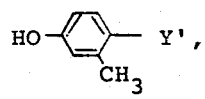

is commercially available and the starting material,

In the above reaction schemes, X and Y are as defined above; Y' is a hydrogen atom or a halogen atom; R' is a hydrogen atom or an alkyl group having 1 to 5 carbon atoms; and R'' is an alkyl group having 1 to 5 carbon atoms or a cation. Further, in the above reaction schemes (I) to (IV), a suitable molar ratio of the reactants is preferably an about stoichiometric ratio. However, molar ratios which vary somewhat, e.g., ±10% from the stoichiometric can also be used if desired.

When a suitable solvent or catalyst is used in the above reactions, the reaction can be carried out more uniformly and within shorter periods of time, and the product can be obtained in a higher yield. For example, in the condensation step, a copper type catalyst is preferably used as a catalyst. Examples of such copper type catalysts include copper powder, a copper-zinc mixture, cupric chloride, cuprous chloride, cupric oxide, cuprous oxide, etc. In the oxidation step, a solvent such as formic acid, propionic acid, acetic acid, etc., can be used in an appropriate amount, with acetic acid being preferred. Further, in the halogenation step, a halogenated methane such as dichloromethane, chloroform, carbon tetrachloride, etc., can be used, with chloroform and carbon tetrachloride being preferred.

Some examples of the synthesis of the compounds in accordance with this invention are given below. In the Synthesis Examples and Examples given herein, all parts, percentages, ratios and the like are by weight.

SYNTHESIS EXAMPLE 1

Preparation of 2,6-Dichloro-4-trifluoromethyl-3'-carbomethoxy-4'-bromodiphenyl ether:

36.5g of 2,6-dichloro-4-trifluoromethyl-3'-carbomethoxy diphenyl ether was dissolved in 200ml of glacial acetic acid, and the solution was maintained at the reflux temperature. 32g of bromine was gradually added to the solution over the course of 1 to 2 hours. When gas-chromatography showed that all of the starting materials had reacted, the reaction was stopped. The product was poured into 500ml of water, and extracted with diethyl ether. After removing the ether from the extracted layer, the residue was distilled under reduced pressure to afford 17.7g of the above product having a boiling point of 190° – 195°C/3mmHg.

SYNTHESIS EXAMPLE 2

Preparation of 2,4'-Dichloro-4-trifluoromethyl-3'-carboxydiphenyl ether:

31.6g of 2-chloro-4-trifluoromethyl-3'-carboxydiphenyl ether was dissolved in 200ml of glacial acetic acid, and the solution was maintained at the reflux temperature. Chlorine gas was bubbled into the solution for 5 hours to chlorinate the diphenyl ether. The reaction mixture was poured into a suitable amount of water to precipitate the product. The resulting crystals were separated by filtration, washed with water, and dried to afford 15.8g of the above product having a melting point of 98° to 106°C.

SYNTHESIS EXAMPLE 3

Preparation of 2,4'-Dichloro-4-trifluoromethyl-3'-carbomethoxydiphenyl ether:

66g of 2,4'-dichloro-4-trifluoromethyl-3'-chloroformyl diphenyl ether which can be obtained by reacting 2,4'-dichloro-4-trifluoromethyl-3'-carboxydiphenyl ether obtained in Synthesis Example 2 with thionyl chloride, and 11.5g of methanol were dissolved in 100ml of benzene. 22g of pyridine was added thereto at a temperature of 20° to 30°C, followed by reacting for 1 hour. The reaction mixture was then poured into a suitable amount of water, followed by extracting with benzene. The extract was washed successively with 2 – 3% hydrochloric acid, 2 – 3% sodium hydroxide and water, and then dried. After removing the benzene, the residue was distilled under reduced pressure to afford 58g of the above product having a boiling point of 186° – 190°C/2mmHg.

Some examples of the compounds of this invention having herbicidal properties are shown in Table 1 below.

Table 1

| No. | Compound | Physical Properties |
|---|---|---|
| 1 | 2,4'-Dichloro-4-trifluoromethyl-3'-carbomethoxy diphenyl ether | b.p. 186–190°C/2mmHg |
| 2 | 2-Chloro-4-trifluoromethyl-3'-carbomethoxy-4'-bromodiphenyl ether | b.p. 185–192°C/2mmHg |
| 3 | 2,6,4'-Trichloro-4-trifluoromethyl-3'-carbomethoxy diphenyl ether | b.p. 180–183°C/3mmHg |
| 4 | 2,6-Dichloro-4-trifluoromethyl-3'-carbomethoxy-4'-bromodiphenyl ether | b.p. 190–195°C/3mmHg |
| 5 | 2,4'-Dichloro-4-trifluoromethyl-3'-carboxy diphenyl ether | m.p. 98–106°C |
| 6 | 2-Chloro-4-trifluoromethyl-3'-carboxy-4'-bromodiphenyl ether | m.p. 85–89°C |
| 7 | 2,6,4'-Trichloro-4-trifluoromethyl-3'-carboxy diphenyl ether | |
| 8 | 2,6-Dichloro-4-trifluoromethyl-3'-carboxy-4'-bromodiphenyl ether | |

The herbicidal properties of the compounds of this invention were tested on plants, and the results obtained are shown in the following.

Test Example 1

Soil was placed in a 0.01m² pot, and the soil was supersaturated with water. Air-dried seeds of barnyard grass were sown in a predetermined amount, and covered lightly with the soil. When the seeds germinated and sprouted above the surface of the soil, the pots were flooded with water to a depth of 3cm, and an aqueous dispersion of each of the Compound Nos. 1 to 8 in the specified concentration was poured into the pots. On the 14th day after the treatment with the solution of the compound of the invention, the surviving barnyard grass was pulled out. This grass was dried in the air, and weighed. The degree of growth was obtained by calculating the percentage of the amount of the surviving barnyard grass based on the amount of the grass in an untreated site.

The results obtained are shown in Table 2.

Table 2

| Compound No. | Degree of Growth (%) Amount of Compound (g/100m²) | |
|---|---|---|
| | 10 | 5 |
| 1 | 0 | 0 |
| 2 | 0 | 0 |
| 3 | 0 | 0 |
| 4 | 0 | 0 |
| 5 | 0 | 0 |
| 6 | 0 | 0 |
| 7 | 0 | 0 |
| 8 | 0 | 0 |
| Untreated (Control) | 100 | |

TEST EXAMPLE 2

Soil was placed in a 0.01m² pot, and the soil was supersaturated with water. Air-dried seeds of barnyard grass were sown in a predetermined amount, and covered lightly with the soil. When the barnyard grass reached the two-leaf stage, the pots were flooded with water to a depth of 4cm, and an aqueous dispersion of each of the Compound Nos. 1 to 4 in a predetermined concentration was poured into the pots. On the 18th day after the treatment with the solution of the compound of the invention, the surviving barnyard grass was pulled out, and the degree of growth was calculated in the same was as in Test Example 1. The results obtained are shown in Table 3.

Table 3

| Compound No. | Degree of Growth (%) Concentrations of the Compound (g/100m$^2$) | | |
|---|---|---|---|
| | 10 | 5 | 2.5 |
| 1 | 0 | 0 | 0 |
| 2 | 0 | 0 | 0 |
| 3 | 0 | 0 | 0 |
| 4 | 0 | 0 | 0 |
| Untreated (Control) | 100 | | |

TEST EXAMPLE 3

Soil was placed in a 0.01m$^2$ pot, and the soil was supersaturated with water. Soil contraining seeds of slender spikerush (*Eleocharis acicularis* Roem et. Shult), monochoria (*Monochoria vaginalis* Presl), toothcup (*Rotala indica* Koehne var. *uliginosa Miquel*) and bulrush (*Scirpus juncoides* Roxburgh var. hotarui Ohwi), etc. was placed on top of the soil in the pot in a thickness of about 5mm. Then, the pots were flooded with water and the depth was maintained at 3cm. On the 7th day, an aqueous dispersion of each of the compounds of this invention in a predetermined concentration was poured into the pots. On the 14th day after the treatment with the solution of the compounds of this invention, the growth of each of these weeds was observed visually. The results obtained are shown in Table 4. The degree of growth inhibition in the table was rated using the following scale with reference to an untreated site as a control.

| Grade | Condition |
|---|---|
| 5 | 100% growth inhibition |
| 4 | About 90% growth inhibition |
| 3 | About 60% growth inhibition |
| 2 | About 30% growth inhibition |
| 1 | Same condition as in the untreated site, with no effect being observed |

Table 4

| Compound No. | Amount (g/100m$^2$) | Degree of Growth Inhibition | | | |
|---|---|---|---|---|---|
| | | Toothcup | Slender Spikerush | Monochoria | Bulrush |
| 1 | 10 | 5 | 5 | 5 | 5 |
| | 5 | 5 | 5 | 5 | 5 |
| 2 | 10 | 5 | 5 | 5 | 5 |
| | 5 | 5 | 5 | 5 | 5 |
| 3 | 10 | 5 | — | 5 | 5 |
| | 5 | 5 | — | 5 | 5 |
| 4 | 10 | 5 | — | 5 | 5 |
| | 5 | 5 | — | 5 | 5 |
| 5 | 10 | 5 | 5 | 5 | 4 |
| | 5 | 5 | 4 | 4 | 3 |
| 6 | 10 | 5 | 4 | 5 | 4 |
| | 5 | 5 | 3 | 5 | 4 |
| 7 | 10 | 5 | 4 | 5 | 4 |
| | 5 | 5 | 4 | 5 | 3 |
| 8 | 10 | 5 | 4 | 4 | 4 |
| | 5 | 5 | 3 | 4 | 4 |

TEST EXAMPLE 4

Soil was placed in a 1/30m$^2$ pot to provide an upland field condition, and predetermined amounts of barnyard grass seeds were sown. The top surface of the soil was then covered with soil containing general weed seeds such as wild barnyard grass, wavy bittercress (*Cardamine flexuosa* Withering), bog stitch wort (*Stellaria uliginosa* Murray var. undulata Franchet et Savalier), and toothcup (*Rotala indica* Koehne var. uliginosa Miquel), etc. to a thickness of about 2cm. On the 3rd day after sowing, an aqueous dispersion of each of the compounds of this invention in predetermined concentrations was sprayed onto the pots. On the 14th day after the treatment with the solution of the compounds of this invention, the growth of each of the weeds was observed visually. The results were graded in the same way as in Test Example 3. The results obtained are shown in Table 5.

Table 5

| Compound No. | Amount (g/100m$^2$) | Degree of Growth Inhibition | |
|---|---|---|---|
| | | Barnyard Grass | General Weeds |
| 1 | 100 | 5 | 5 |
| | 50 | 5 | 5 |
| 2 | 100 | 5 | 5 |
| | 50 | 5 | 5 |
| 3 | 100 | 5 | 5 |
| | 50 | 5 | 5 |
| 4 | 100 | 5 | 5 |
| | 50 | 5 | 5 |
| 5 | 100 | 5 | 5 |
| | 50 | 5 | 5 |
| 6 | 100 | 5 | 5 |
| | 50 | 5 | 5 |
| 7 | 100 | 5 | 5 |
| | 50 | 5 | 5 |
| 8 | 100 | 5 | 5 |
| | 50 | 5 | 5 |

TEST EXAMPLE 5

Soil was placed in a 0.01m$^2$ pot to provide an upland field condition. A predetermined amount of seeds of barnyard grass was sown, and covered with soil in a thickness of about 1cm. When the barnyard grass reached the two-leaf stage, an aqueous dispersion of each of the compounds of this invention in predetermined concentrations was applied to the foliage in a predetermined amount, i.e., 15l/100m$^2$. On the 14th day after the treatment, the growth of the barnyard grass was observed visually, and rated using the same criteria as in Test Example 3. The results obtained are shown in Table 6.

Table 6

| Compound No. | Degree of Growth Inhibition Concentration of the Compound (ppm) | |
|---|---|---|
| | 2000 | 1000 |
| 1 | 5 | 5 |
| 2 | 5 | 5 |
| 3 | 5 | 5 |
| 4 | 5 | 5 |
| 5 | 5 | 5 |
| 6 | 5 | 5 |
| 7 | 5 | 5 |
| 8 | 5 | 5 |

TEST EXAMPLE 6

Soil was placed in a 1/9m$^2$ pot to provide an upland field condition, and predetermined amounts of various crop seeds were sown. The top surface of the soil was then covered with soil containing various weed seeds to a thickness of about 2cm. On the 3rd day after sowing, an aqueous dispersion containing the compounds of this invention was sprayed onto the pot. On the 20th day after the treatment with the solution of the compounds of this invention, the growth of each of the crops and weeds was observed visually. The results obtained are shown in Table 7 below. In the table, a numerical value of 10 shows that the growth of the crops and weeds was completely inhibited. Hereinafter, the degree of growth inhibition in the table is described in ten stages.

The compounds of this invention can also be used together with agricultural chemicals such as other herbicides or fungicides or other controlling agents, and also with a fertilizer or soil. Sometimes, the combined use of the compounds of this invention with these gives rise to better effects.

The following non-limiting Examples are given to further illustrate the present invention.

Table 7

| Compound No. | Amount (g/100m²) | Degree of Growth Inhibition |||||||||||||||||
|---|---|---|---|---|---|---|---|---|---|---|---|---|---|---|---|---|---|---|
| | | Crops |||||||||||||| Weeds |||
| | | A | B | C | D | E | F | G | H | I | J | K | L | M | N | O | P | Q | R |
| 1 | 20 | 5 | 10 | 6 | 7 | 6 | 10 | 3 | 1 | 7 | 5 | 9 | 10 | 9 | 9 | 7 | 10 | 10 | 10 |
|   | 10 | 2 | 10 | 3 | 4 | 5 | 7 | 3 | 1 | 6 | 3 | 6 | 9 | 6 | 8 | 7 | 10 | 10 | 10 |
|   | 5  | 2 | 7  | 2 | 2 | 4 | 5 | 3 | 1 | 5 | 3 | 5 | 6 | 5 | 8 | 5 | 10 | 10 | 10 |
| 2 | 20 | 4 | 9  | 5 | 6 | 7 | 8 | 10 | 4 | 10 | 5 | 10 | 10 | 8 | 8 | 7 | 10 | 10 | 10 |
|   | 10 | 3 | 8  | 5 | 6 | 6 | 8 | 10 | 3 | 8 | 4 | 7 | 8 | 6 | 7 | 7 | 10 | 10 | 10 |
|   | 5  | 2 | 5  | 3 | 4 | 4 | 4 | 10 | 2 | 6 | 3 | 7 | 7 | 6 | 7 | 6 | 10 | 10 | 10 |
| 3 | 20 | 5 | 9  | 6 | 6 | 6 | 8 | 5 | 5 | 10 | 5 | 9 | 10 | 6 | 8 | 8 | 10 | 10 | 10 |
|   | 10 | 4 | 7  | 5 | 5 | 5 | 7 | 2 | 3 | 6 | 5 | 6 | 9 | 4 | 7 | 7 | 10 | 10 | 10 |
|   | 5  | 2 | 7  | 4 | 4 | 5 | 5 | 2 | 2 | 6 | 2 | 5 | 7 | 3 | 5 | 6 | 10 | 10 | 10 |
| 4 | 20 | 5 | 10 | 6 | 7 | 7 | 10 | 7 | 5 | 10 | 8 | 10 | 10 | 7 | 10 | 10 | 10 | 10 | 10 |
|   | 10 | 3 | 10 | 6 | 7 | 6 | 7 | 6 | 5 | 10 | 6 | 7 | 10 | 6 | 9 | 9 | 10 | 10 | 10 |
|   | 5  | 3 | 7  | 4 | 4 | 4 | 5 | 4 | 3 | 7 | 3 | 6 | 7 | 6 | 9 | 7 | 10 | 10 | 10 |

NOTE:
A: Soy bean  E: Two-rowed barley  I: Radish     M: Cabbage
B: Red bean  F: Beet               J: Egg-plant  N: Lettuce
C: Maize     G: Burdock            K: Flax       O: Cucumber
D: Wheat     H: Sunflower          L: Tomato     P: Large crab-grass
                                                 Q: Wild barnyard grass
                                                 R: Broad leaved weeds The compounds in accordance with this invention having herbicidal properties can be directly used in the form of an aqueous dispersion as shown in the above test examples. The compounds of this invention can further be used in various herbicidal compositions in the form of a dust, granules, a wettable powder, a water-miscible solution or an emulsion together with various additives such as a diluent, a solvent, an emulsifier or a dispersing agent, and also can be used by diluting with water.

Examples of diluents which can be used are inert organic solvents such as xylene, toluene, chlorobenzene, cyclohexane, alcohols, methyl ethyl ketone, solvent naphtha, isophorone, etc., and solid carriers such as vermiculite, attapulgite, bentonite, talc, clay, kaolin, diatomaceous earth, white carbon, etc. Examples of emulsifiers which can be used include a sodium alkylbenzenesulfonate, a polyoxyethylene aliphatic alcohol ester, an alkylsulfonate, etc. Further, examples of dispersing agents which can be used include calcium ligninsulfonate, a sodium alkylbenzene sulfonate, waste ligninsulfite, methyl cellulose, etc.

The compositions of this invention can be applied to a wide variety of sites such as rice paddies, farm land, orchards, mulberry fields, woods or forests, agricultural roads, grounds, or factory lots for soil treatment and foliage treatment both in flooded and upland conditions. The suitable amount of the compounds of this invention to be applied cannot be set forth unequivocally since it may vary according to the weather conditions, the soil conditions, the herbicidal formulation in which the compounds of the invention is employed, the time of application, the method of application, or the type of weed to be controlled, etc. Generally, however, a suitable amount is about 1 to 100g, preferably 3 to 50g, most preferably 5 to 30g, per 100m² of the site to be treated.

EXAMPLE 1

| | | Parts by Weight |
|---|---|---|
| (a) | 2,4'-Dichloro-4-trifluoromethyl-3'-carbomethoxy diphenyl ether | 20 |
| (b) | Sorpol 2806 B (Tradename for a mixture of a polyoxyethylene phenylphenol derivative, a polyoxyethylene alkylaryl ether, a polyoxyethylene sorbitan alkylate and an alkylaryl sulfonate produced by Toho Chemical Co., Ltd.) | 20 |
| (c) | Xylene | 60 |

The above ingredients were uniformly mixed to form a herbicidal composition in the form of an emulsifiable concentrate.

EXAMPLE 2

| | | Parts by Weight |
|---|---|---|
| (a) | 2-Chloro-4-trifluoromethyl-3'-carboxy-4'-bromodiphenyl ether | 10 |
| (b) | Bentonite | 85 |
| (c) | Sodium Ligninsulfonae | 5 |

These ingredients were mixed together with a suitable amount of water to form a granular herbicidal composition.

EXAMPLE 3

| | | Parts by Weight |
|---|---|---|
| (a) | 2-Chloro-4-trifluoromethyl-3'-carbomethoxy-4'-bromodiphenyl ether | 40 |
| (b) | Kaolin | 55 |
| (c) | Sodium Alkylbenzene Sulfonae | 2.5 |
| (d) | White Carbon | 2.5 |

A mixture of the above ingredients (c) and (d) was mixed with (b), and further, these materials were uniformly mixed with (a) to form a herbicidal composition in the form of a wettable powder.

While the invention has been described in detail and with reference to specific embodiments thereof, it will be apparent to one skilled in the art that various changes and modifications can be made therein without departing from the spirit and scope thereof.

What we claim is:

1. A compound of the general formula (I)

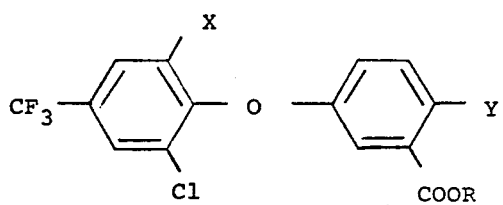

(I)

wherein X is a hydrogen atom or a chlorine atom; Y is a halogen atom; and R is a hydrogen atom, an alkyl group containing 1 to 5 carbon atoms, or a cation.

2. The compound of claim 1, wherein X is a hydrogen atom.
3. The compound of claim 1, wherein X is a chlorine atom.
4. The compound of claim 2, wherein R is a methyl group.
5. The compound of claim 3, wherein R is a methyl group.
6. The compound of claim 1, wherein said compound of the general formula (I) is 2,4'-dichloro-4-trifluoromethyl-3'-carbomethoxydiphenyl ether.
7. The compound of claim 1, wherein said compound of the general formula (I) is 2-chloro-4-trifluoromethyl-3'-carbomethoxy-4'-bromodiphenyl ether.
8. The compound of claim 1, wherein said compound of the general formula (I) is 2,6,4'-trichloro-4-trifluoromethyl-3'-carbomethoxydiphenyl ether.
9. The compound of claim 1, wherein said compound of the general formula (I) is 2,6-dichloro-4-trifluoromethyl-3'-carbomethoxy- 4'-bromodiphenyl ether.
10. The compound of claim 1, wherein said compound of the general formula (I) is 2,4'-dichloro-4-trifluoromethyl-3'-carboxydiphenyl ether.
11. The compound of claim 1, wherein said compound of the general formula (I) is 2-chloro-4-trifluoromethyl-3'-carboxy-4'-bromodiphenyl ether.
12. The compound of claim 1, wherein said compound of the general formula (I) is 2,6,4'-trichloro-4-trifluoromethyl-3'-carboxydiphenyl ether.
13. The compound of claim 1, wherein said compound of the general formula (I) is 2,6-dichloro-4-trifluoromethyl-3'-carboxy-4'-bromodiphenyl ether.

* * * * *